United States Patent
Ivanovic et al.

(10) Patent No.: US 8,366,611 B2
(45) Date of Patent: Feb. 5, 2013

(54) ENDOSCOPE WITH SEALING RING

(75) Inventors: Boban Ivanovic, Tuttlingen (DE); Nicolino Caruso, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 539 days.

(21) Appl. No.: 12/640,271

(22) Filed: Dec. 17, 2009

(65) Prior Publication Data

US 2010/0160734 A1    Jun. 24, 2010

(30) Foreign Application Priority Data

Dec. 18, 2008  (DE) .................. 10 2008 063 619

(51) Int. Cl.
*A61B 1/00*    (2006.01)

(52) U.S. Cl. ....................... 600/176; 600/129

(58) Field of Classification Search .............. 600/133, 600/129, 171, 172, 176; 359/513
See application file for complete search history.

(56) References Cited

U.S. PATENT DOCUMENTS

| | | | |
|---|---|---|---|
| 4,576,147 A * | 3/1986 | Hashiguchi ............... 600/129 |
| 4,850,342 A * | 7/1989 | Hashiguchi et al. ......... 600/171 |
| 4,916,534 A * | 4/1990 | Takhashi et al. ............... 348/67 |
| 5,177,641 A * | 1/1993 | Kobayashi et al. ........... 359/820 |
| 5,377,669 A | 1/1995 | Schulz | |
| 5,894,369 A * | 4/1999 | Akiba et al. ................. 359/820 |
| 6,146,326 A * | 11/2000 | Pollack et al. ................. 600/141 |
| 6,503,196 B1 * | 1/2003 | Kehr et al. ..................... 600/176 |
| 6,547,721 B1 * | 4/2003 | Higuma et al. ............... 600/133 |
| 6,821,246 B2 | 11/2004 | Kasel et al. | |
| 6,918,673 B2 * | 7/2005 | Johnson et al. ............... 359/513 |
| 7,699,773 B2 * | 4/2010 | Forkey et al. ................. 600/172 |
| 7,751,131 B2 * | 7/2010 | Huang et al. ................. 359/819 |
| 8,169,724 B2 * | 5/2012 | Hirata et al. .................. 359/827 |
| 2001/0039371 A1 * | 11/2001 | Forster ......................... 600/176 |
| 2008/0242927 A1 | 10/2008 | Hirata | |

\* cited by examiner

*Primary Examiner* — John P Leubecker

(74) *Attorney, Agent, or Firm* — Skaar Ulbrich Macari, P.A.

(57) ABSTRACT

An endoscope having an endoscope shaft is provided, which has an observation opening on its distal end, which is hermetically sealed using a transparent cover, and having an imaging optic, comprising multiple optic elements, which is situated inside the endoscope shaft in the area of its distal end spaced apart from the cover, a sealing ring being provided, which seals an area between the cover and the optic element of the imaging optic closest to the cover in relation to the remaining inner chamber of the endoscope shaft.

15 Claims, 1 Drawing Sheet

ENDOSCOPE WITH SEALING RING

PRIORITY

The present application claims benefit of German Application No. 102008063619.3, filed Dec. 18, 2008, the disclosure of which is hereby incorporated by reference.

FIELD

The present invention relates to an endoscope having an endoscope shaft, which has an observation opening on its distal end, which is closed hermetically sealed using a transparent cover, and having an imaging optic comprising multiple optic elements, which is situated inside the endoscope shaft in the area of its distal end spaced apart from the cover.

BACKGROUND

In conventional endoscopes, for example the endoscope disclosed in DE 42 11 547 A1, the difficulty exists that contaminants may collect on the inner side of the cover and on the optic element of the imaging optic closest to the cover, which significantly worsen the imaging quality. Such contaminants may particularly occur due to the required autoclaving, in which the endoscope or at least the shaft is sterilized for multiple minutes in saturated water steam at up to 140° C. These conditions may result in contaminants detaching from the interior of the endoscope shaft, accumulating, and thus leading to undesired worsening in the imaging, for example.

SUMMARY

It is an object of certain embodiments of the invention to refine an endoscope with good imaging properties may be permanently ensured.

In certain embodiments, this object is achieved in an endoscope in that the area between the cover and the optic element of the imaging optic closest to the cover is sealed in relation to the remaining inner chamber of the endoscope shaft using a sealing ring. Using such a sealing ring, contaminants can be reliably prevented from being able to penetrate into the intermediate space. The sealing ring can press against the inner side of the cover facing toward the imaging optic. Furthermore, the sealing ring can press against the circumference of the optical element closest to the cover. A very compact construction is thus implemented, in which the contamination of the intermediate space can be reliably avoided. Furthermore, the sealing ring can also be used as a scattered light guard for the optic element closest to the cover, because it shadows the light exiting around the circumference.

The sealing ring in one embodiment is elastic. It can be produced from an elastic polymer, such as ethylene-propylene-diene caoutchouc, silicone, Teflon, fluoroelastomers, or fluorinated caoutchouc.

The sealing ring can be used as a damping element between cover and imaging optic, which protects the imaging optic due to its damping property in the event of impacts against the cover, for example.

The sealing ring can have the form of a circular ring, an oval, or another form which is closed per se. It is essential that it securely seals the intermediate space.

The imaging optic can be displaceable relative to the cover in the axial direction. Differing expansions during the autoclaving may thus be taken into consideration. In this case, the sealing ring is used for tolerance compensation, so that the intermediate space is always securely sealed even during these differing length changes.

The endoscope shaft can have an outer tube and an inner tube situated in the outer tube, on whose distal end the observation opening is implemented. In particular, the imaging optic can be seated in an optic tube which is situated in the inner tube.

The sealing ring in additional example embodiments can be implemented as an O-ring or as a ring having an oval or round cross-section. However, any other ring cross-section is possible, for example square, rectangular, polygonal, etc.

In the endoscope according an example embodiment, a carrier can be situated at the distal end, which has a central opening, which forms the observation opening. The central opening is closed hermetically sealed using the transparent cover. The carrier is preferably not transparent and is in turn connected hermetically sealed to the endoscope shaft or to the inner tube, for example. The sealing ring can press against the carrier instead of the cover.

The endoscope according to an example embodiment can be implemented as an endoscope having a rigid or flexible endoscope shaft. In particular, the endoscope can be a medical endoscope. Furthermore, an image sensor can be situated directly behind the imaging optic, so that a very compact image recording module can be implemented at the distal end of the endoscope shaft.

The endoscope according to the example embodiments and claims recited herein may have further elements known to those skilled in the art, which are required for the intended use of the endoscope.

It is understood that the above-mentioned features and the features still to be explained hereafter are usable not only in the disclosed combinations, but rather also in other combinations or alone, without leaving the scope of the present invention.

BRIEF DESCRIPTION OF THE DRAWINGS

The invention will be commented on in greater detail hereinafter by way of example with reference to the appended drawings in which:

FIG. 1 shows a schematic illustration of an example embodiment of the, and

DETAILED DESCRIPTION

Figure 1:
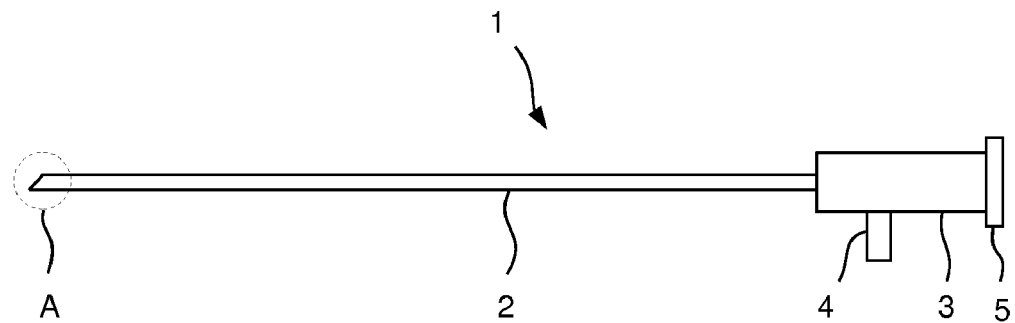
Figure 2:
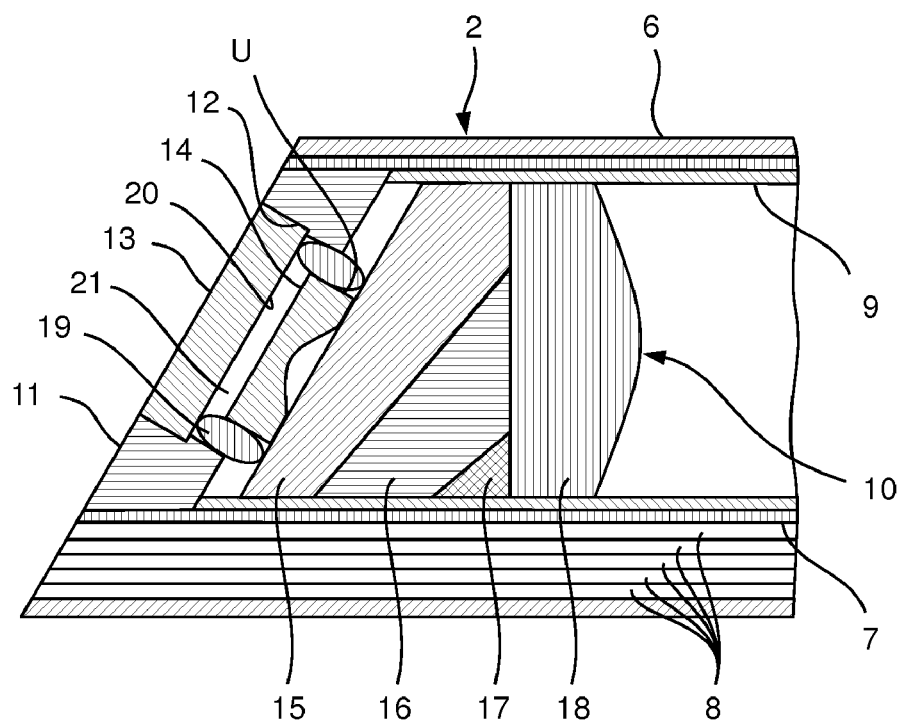
FIG. 2 shows an enlarged sectional illustration of detail A from FIG. 1.

In the example embodiment shown in FIGS. 1 and 2, the endoscope 1 comprises an endoscope shaft 2, which is connected at its proximal end to a main body 3. The main body 3 has an optical fiber connection 4 and an adapter 5 for connecting a camera (not shown) to the main body 3.

As can be appreciated from the enlarged sectional illustration of the distal end of the endoscope shaft 2 in FIG. 2 in particular, the endoscope shaft 2 has an outer tube 6, in which an inner tube 7 having smaller diameter is inserted. Schematically shown optical fibers 8 are situated in the area between outer and inner tubes 6, 7.

An optic tube 9, which carries an imaging optic 10 on its distal end, is situated inside the inner tube 7. The distal end of the optic tube 9 is somewhat put back, together with the imaging optic 10, in relation to the distal end of inner and outer tubes 7, 8. In the area of the distal end of the inner tube 7, a nontransparent carrier 11 is connected hermetically sealed (i.e. sealed during autoclaving) to the inner side of the inner tube 7. The carrier 11 has a central opening 12, which is implemented as stepped when viewed in cross-section. A transparent cover 13 (in the form of a sapphire glass here) is inserted in the central opening 12 and soldered to the carrier 11, so that the central opening 12 and thus the distal end of the inner tube 7 are closed hermetically sealed. The central opening 12 is used as the observation opening for the imaging optic 10.

The imaging optic 10 has, as is evident from FIG. 2, five optic elements 14, 15, 16, 17, and 18, of which the optic elements 15-18 are connected to the inner side of the optic tube 9. Because the optic tube 9 has a circular cross-section and the optic elements 15-17 do not have a circular cross-section, there is an intermediate space in a direction perpendicular to the plane of the drawing of FIG. 2 between the optic elements 15-18 and the optic tube 9. In order to avoid undesired scattered light, which can escape laterally from the optic elements 14-18, the edges of the optic elements 14-18 are blackened. The first optic element 14, which is situated closest to the cover 13 and is a negative or diverging lens here, is glued to the second optic element 15.

An annular sealing ring or gasket 19 is situated around the first optic element 14, which presses against the circumference or edge U of the first optic element 14 on the one hand and against the inner side 20 of the cover 13 on the other hand. The intermediate space 21 between the inner side 20 and the first optic element 14 is thus sealed in relation to the remaining inner chamber of the optic tube 9. Contaminants can thus advantageously be prevented from reaching the intermediate space 21 from the proximal side (i.e., from the right in FIG. 2) from the inner tube 7 or the optic tube 9, which would interfere greatly in the optical imaging. In particular, flakes of the blackening material of the edges of the optic elements 14-18 may not reach the intermediate space 21.

Furthermore, the sealing ring 19 is used for scattered light suppression in the first optic element 14 and is used for tolerance compensation during autoclaving, when the optic tube 9 having the imaging optic 10 expands differently in the axial direction than outer and inner tubes 6, 7 together with the carrier 11 and the cover 13. The sealing ring 19 is produced from an elastic polymer, which is selected so that it is resistant at the temperatures which occur during autoclaving.

Using the endoscope 1, an object situated in front of the distal end can be imaged on an image sensor, which is either situated directly behind the imaging optic 10 (i.e., to the right thereof in FIG. 2) or on the adapter 5, through the cover 13 using the imaging optic 10, which can also be referred to as a compact objective. In the latter case, still further optics, such as known rod lenses, may be situated between the imaging optic 10 and the main body 3 inside the endoscope shaft 2.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

What is claimed is:

1. An endoscope comprising:
    an endoscope shaft having an observation opening on a distal end and an inner chamber;
    a transparent cover configured to hermetically seal the distal end;
    an imaging optic disposed in the inner chamber, comprising multiple optic elements, situated inside the endoscope shaft adjacent the distal end and spaced apart from the cover to form an area between the transparent cover and a first of the multiple optic elements; and
    a sealing ring disposed between the transparent cover and the first of the multiple optic elements of the imaging optic situated closest to the cover to seal the area between the transparent cover and the first of the multiple optic elements in relation to the remaining inner chamber of the endoscope shaft,
    wherein the sealing ring presses against an inner side of the cover facing toward the imaging optic and against a circumferential edge of the first of the multiple optic elements.

2. The endoscope according to claim 1, wherein the sealing ring is elastic.

3. The endoscope according to claim 1, wherein the imaging optic is displaceable in relation to the cover in the axial direction.

4. The endoscope according to claim 1, wherein the endoscope shaft includes an outer tube and an inner tube, the inner tube being located in the outer tube and having a distal end defining an observation opening.

5. The endoscope according to claim 4, wherein the imaging optic is disposed in an optic tube, the optic tube being located in the inner tube.

6. The endoscope according to claim 1, wherein the sealing ring is an O-ring.

7. The endoscope according to claim 1, further comprising a non-transparent carrier disposed in a portion of the inner chamber, the carrier defining a recess therein configured to receive the transparent cover.

8. The endoscope of claim 7, wherein the sealing ring contacts an inner circumference of the non-transparent carrier.

9. The endoscope of claim 7, wherein the sealing ring further contacts a second of the multiple optic elements.

10. The endoscope of claim 1, wherein the sealing ring further contacts a second of the multiple optic elements.

11. An endoscope comprising:
    an endoscope shaft having an observation opening on a distal end and an inner chamber;
    a transparent cover configured to hermetically seal the distal end;
    an imaging optic disposed in the inner chamber, comprising multiple optic elements, situated inside the endoscope shaft adjacent the distal end and spaced apart from the cover to form an area between the transparent cover and a first of the multiple optic elements; and
    an elastic sealing ring disposed between the transparent cover and the first of the multiple optic elements of the imaging optic situated closest to the cover to seal the area between the transparent cover and the first of the multiple optic elements in relation to the remaining inner chamber of the endoscope shaft,
        wherein the sealing ring further contacts a second of the multiple optic elements.

12. The endoscope of claim 11, wherein wherein the sealing ring presses against an inner side of the cover facing toward the imaging optic and against the first of the multiple optic elements.

13. The endoscope of claim 11, wherein the sealing ring contacts an inner circumference of a non-transparent carrier, the carrier defining a recess therein configured to receive the transparent cover.

14. An endoscope comprising:
- an endoscope shaft having an observation opening on a distal end and an inner chamber;
- a transparent cover configured to hermetically seal the distal end;
- an imaging optic disposed in the inner chamber, comprising multiple optic elements, situated inside the endoscope shaft adjacent the distal end and spaced apart from the cover to form an area between the transparent cover and a first of the multiple optic elements; and
- a sealing ring disposed between the transparent cover and the first of the multiple optic elements of the imaging optic situated closest to the cover to seal the area between the transparent cover and the first of the multiple optic elements in relation to the remaining inner chamber of the endoscope shaft, wherein the sealing ring presses against an inner side of the cover facing toward the imaging optic and against the first of the multiple optic elements,
- wherein the sealing ring contacts an inner circumference of the non-transparent carrier, the carrier defining a recess therein configured to receive the transparent cover.

15. The endoscope of claim 14, wherein the sealing ring further contacts a second of the multiple optical elements.

* * * * *